United States Patent [19]

Henrick et al.

[11] 4,178,293

[45] Dec. 11, 1979

[54] ISOINDOLINYL DERIVATIVES

[75] Inventors: Clive A. Henrick; Robert L. Carney; Jeffrey N. Labovitz, all of Palo Alto, Calif.

[73] Assignee: Zoecon Corporation, Palo Alto, Calif.

[21] Appl. No.: 915,045

[22] Filed: Jun. 12, 1978

Related U.S. Application Data

[63] Continuation-in-part of Ser. No. 896,261, Apr. 14, 1978, abandoned.

[51] Int. Cl.$^2$ .................. A01N 9/22; C07D 209/44; C07D 217/04
[52] U.S. Cl. .................. 260/326.1; 260/651 R; 260/651 F; 546/143; 546/145; 546/146; 424/258; 424/274; 568/811
[58] Field of Search .................. 260/326.1, 287 D

[56] References Cited

U.S. PATENT DOCUMENTS

| 3,483,206 | 12/1969 | Werner | 260/287 D |
| 3,997,669 | 12/1976 | Carney | 424/274 |

*Primary Examiner*—Alton D. Rollins
*Attorney, Agent, or Firm*—Donald W. Erickson

[57] ABSTRACT

Esters of lower alkanoic acids substituted at the α-position with isoindoline or tetrahydroisoquinoline, and intermediates therefor, useful as pesticides.

18 Claims, No Drawings

ISOINDOLINYL DERIVATIVES

This is a continuation-in-part of Ser. No. 896,261, filed Apr. 14, 1978, now abandoned the entire disclosure of which is incorporated herein by reference.

This invention relates to novel esters of lower alkanoic acids substituted at the alpha position with isoindoline, substituted isoindoline, 1,2,3,4-tetrahydroisoquinoline, or substituted 1,2,3,4-tetrahydroisoquinoline, synthesis thereof and intermediates therefor.

More particularly, the novel compounds of the present invention are represented by the following formula (A):

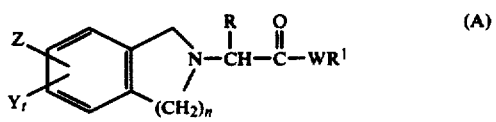

wherein,
n is one or two;
t is zero, one, two or three;
W is oxygen or sulfur;
Y is independently selected from hydrogen, lower alkyl, lower haloalkyl, lower alkoxy, lower alkylthio, lower alkyl-carbonyl, lower alkoxycarbonyl, lower aryloxy, halogen, cyano, nitro and lower haloalkylthio;
Z is independently selected from the values of Y, cycloalkyl, and lower haloalkoxy; or together with Y forms a methylenedioxy group;
R is lower alkyl of 2 to 5 carbon atoms; and
$R^1$ is the group

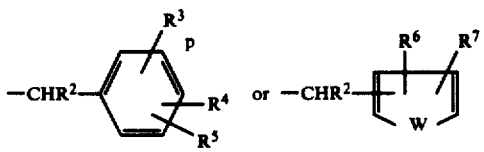

in which,
p is zero, one, two or three;
$R^2$ is hydrogen, cyano, methyl or ethynyl;
$R^3$ is halogen, lower alkyl, lower haloalkyl, lower alkoxy, lower haloalkoxy, lower alkylthio, lower alkenyl, or lower haloalkenyl;
$R^4$ is hydrogen or together with $R^3$ forms a lower alkylenedioxy bridge across adjacent ring carbon atoms;
$R^5$ is hydrogen, lower alkenyloxy, lower alkynyl, lower alkynyloxy, lower haloalkynyl, lower alkylcarbonyl, arylcarbonyl, substituted arylcarbonyl, aryloxy, substituted aryloxy, arylthio, substituted arylthio, aralkyl, substituted aralkyl, cycloalkyl, cycloalkalkyl, lower acyloxy, aryloxycarbonyl, lower alkoxycarbonyl, or lower haloalkenyloxy;
$R^6$ is hydrogen or lower alkyl;
$R^7$ is lower alkenyl, lower alkynyl, or aralkyl, and the salts thereof of strong inorganic acids or organic acids.

The compounds of the present invention represented by generic formula (A) are useful agents for the control of pests such as insects and acarids. Without any intention of being bound by theory and although the mode of action of the compounds of formula (A) as applied to the control of insects and acarids is not completely understood, the compounds of formula (A) appear to be effective for the control of insects and acarids by reason of mechanisms of the nature of the insect control agents known as pyrethrins and synthetic pyrethroids.

In the description hereinafter and the appended claims, each of R through $R^7$, W, Y, Z, n, p, and t is as defined hereinabove, unless othersie specified.

The compounds of formula (A) can be synthesized by the reaction of a dibromide of formula I, or the corresponding dichloride thereof, with an amino ester of formula II.

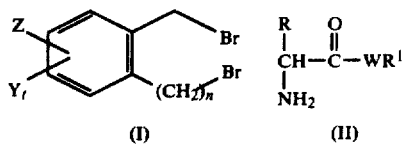

The reaction of I and II is carried out in the presence of a base such as potassium carbonate in a solvent such as hexamethylphosphoric triamide, dimethylformamide, tetrahydrofuran, and the like. The reaction is generally conducted at room temperature.

The compounds of formula A can be synthesized also by the reaction of an amine of formula III with an α-bromo acid or salt thereof of formula IV.

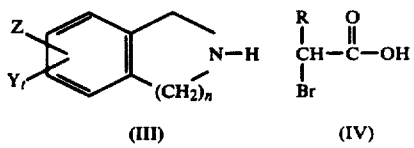

The reaction is carried out in a solvent such as the above with the acid in the form of its salt such as the sodium or potassium salt at above room temperature, such as the reflux temperature of the reaction mixture. Thereafter, the amino substituted acid or salt thereof is esterified to obtain the ester (A).

The following terms, wherever used in the description herein and the appended claims, have the meaning defined below, unless otherwise specified hereinafter.

The term "lower alkyl" refers to an alkyl group, straight or branched, having a chain length of one to six carbon atoms. The term "lower haloalkyl" refers to an alkyl group substituted with one to three halogen atoms such as chloromethyl, fluoromethyl, trifluoromethyl, 2,2,2-trifluoroethyl, 6-chlorohexyl, 2-fluoroethyl, and the like. The term "lower alkoxy" refers to an alkoxy group, straight or branched, having a chain length of one to six carbon atoms. The term "lower alkylthio" refers to an alkylthio group, straight or branched, having a chain length of one to six carbon atoms.

The term "lower alkenyl" refers to an ethylenically unsaturated hydrocarbon group, straight or branched, having a chain length of two to six carbon atoms and one or two ethylenic bonds such as vinyl, allyl, 3-butenyl, 2-hexenyl, i-propenyl, 2,4-hexadienyl, and the like. The term "lower haloalkenyl" refers to a lower alkenyl group substituted with one to three halogen atoms. The term "lower alkenyloxy" refers to an alkenyloxy group, straight or branched, of two to six carbon atoms. The term "lower haloalkenyloxy" refers to a lower alkenyloxy group substituted with one to three halogen atoms.

The term "lower alkynyl" refers to an alkynyl group, straight or branched, having a chain length of two to six carbon atoms and one or two acetylenic bonds. The term "lower haloalkynyl" refers to a lower alkynyl group having one to three halogen atoms. The term "lower alkynyloxy" refers to an alkynyloxy group, straight or branched, of three to six carbon atoms.

The term "cycloalkyl" refers to a cycloalkyl group of three to six cyclic carbon atoms. The term "cycloalkalkyl" refers to a cycloalkyl group wherein one hydrogen atom is replaced by a lower alkyl group, the total number of carbon atoms being from four to eight, such as cyclopropanemethyl, cyclobutaneethyl, cyclohexanemethyl, and the like.

The term "aryl" refers to the aryl group phenyl or naphthyl. The term "aralkyl" refers to a lower alkyl group in which a hydrogen atom of the alkyl group is substituted by an aryl group, the total number of carbon atoms being from seven to twelve, such as benzyl, phenethyl, and the like. The terms "substituted aryl" and "substituted aralkyl" refer to an aryl group and an aralkyl group, respectively, substituted at one, two or three of the ring carbon atoms with a group selected from lower alkyl, lower haloalkyl, lower alkoxy, lower alkenyl, lower haloalkenyl, lower alkenyloxy, halogen, nitro, cyano, lower alkylthio, and the like.

The term "lower haloalkoxy" refers to a lower alkoxy group substituted with one to three halogen atoms.

The term "lower acyloxy" refers to a lower organic acyloxy group of one to six carbon atoms, such as acetoxy.

The compounds of the present invention of formula (A) have one or more asymmetric carbon atoms. The present invention includes each of the optical isomers and racemic mixtures thereof. In the examples hereinafter, unless otherwise specified, the compound prepared in a racemic mixture.

Included within the present invention are salts of the compounds of formula A. The salts are formed from strong inorganic acids or organic acids such as hydrochloric acid, sulfuric acid, phosphoric acid, p-toluenesulfonic acid, p-benzenesulfonic acid, methanesulfonic acid, Lewis acid and the like. Many of the compounds of formula A are oils which advantageously are converted into the salt for convenience of handling and formulating and superior stability. The salts are useful for the control of pests in the same way as the compounds of formula A.

The compounds of the present invention of formula A are useful pest control agents, particularly for the control of insects and acarids. In the use of the compounds of formula A for combating insects and acarids for the protection of agricultural crops, for example soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 percent, by weight.

As shown hereinafter, the compounds of the present invention are effective on many different insects and on acarids. The compounds are effective control agents for insects such as mosquitoes, flies, aphids, weevils and acarids such as the spider mite and ticks. Depending upon the particular combination of the substituents of formula A herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compounds of the present invention can be used in combination with other pesticides such as the carbamates, phosphates and insect growth regulators, e.g. propoxur, carbaryl, naled, dichlorvos, methoprene, kinoprene, hydroprene, cyhexatin and resmethrin.

The following examples are provided to illustrate the practice of the present invention. Temperature is given in degrees Centigrade. RT means room temperature.

EXAMPLE 1

To 10 ml hexamethylphosphoric triamide (HMPT) is added m-phenoxybenzyl ester of valine (1.77 g, 6.0 mmol), potassium carbonate (1.65 g, 12 mmol), and $\alpha,\alpha'$-dibromo-o-xylene (1.77 g, 6.6 mmol). The reaction mixture is stirred at room temperature (RT) for 3 days. The mixture is then poured into ether, and the organic phase washed with water and brine, dried over sodium sulfate and evaporated. The residue is purified by prep. thin layer chromatography (TLC) on silica gel eluting with 10% ethyl acetate/hexane to obtain m-phenoxybenzyl 2-(2-isoindolinyl)-3-methylbutanoate, MS m/e 301.2 (M+).

EXAMPLE 2

To 20 ml dimethylformamide (DMF) is added 1,2-bis(bromoethyl)-4-chlorobenzene (2.9 g, 9.7 mmol), potassium carbonate (4.2 g, 29.1 mmol) and m-phenoxybenzyl ester of valine (4.6 g, 9.7 mmol). The reaction mixture is stirred at RT, under nitrogen, for 18 hours. The reaction mixture is then diluted with ether, and the organic phase washed with water and brine, dried over sodium sulfate and evaporated. The crude product is purified by prep. TLC on silica gel eluting with 15% ethyl ether/hexane to obtain m-phenoxybenzyl 2-(5-chloro-2-isoindolinyl)-3-methylbutanoate, MS m/e 435.2 (M+).

EXAMPLE 3

To 10 ml DMF is added 1,2-bis(bromomethyl)-6-chlorobenzene (2.9 g, 7.8 mmol), potassium carbonate (3.22 g, 23.3 mmol) and m-phenoxybenzyl ester of valine (4.0 g, 8.5 mmol). The reaction mixture is stirred at RT, under nitrogen, for 4 hours. The reaction mixture is then taken up in ether, and the organic phase is washed with water and brine, dried over sodium sulfate and evaporated. The crude product is purified by prep. TLC on silica gel eluting with 15% ethyl ether/hexane, collected and eluted with 20% ethyl ether/hexane to obtain m-phenoxybenzyl 2-(7-chloro-2-isoindolinyl)-3-methylbutanoate, MS m/e 435.2 (M+).

EXAMPLE 4

To 10 ml tetrahydrofuran (THF) is added 3,4,5,6-tetrafluoro-1,2-benzenedicarboxylic acid (2 g, 8.4 mmol). After cooling to 0°, 21.0 ml (20.9 mmol) of 1 M borane in THF is slowly added. The reaction mixture is allowed to rise to RT and stirred at RT for 18 hours and then is cooled and quenched with 10% HCl. The reaction mixture is added to ether, and the organic phase is washed with water, sat. sodium bicarbonate and brine, dried over sodium sulfate and evaporated under vacuum to yield 3,4,5,6-tetrafluoro-1,2-bis(hydroxymethyl)benzene.

To a solution of 3,4,5,6-tetrafluoro-1,2-bis(hydroxymethyl)benzene (1.5 g) in about 20 ml ether, in an ice bath, is slowly added phosphorus tribromide (1.3 g, 5 mmol) in about 10 ml ether. After about 2.5 hours, the reaction mixture is poured into ether (150 ml), and the organic phase is washed with water, dried over sodium sulfate and solvent evaporated to yield 3,4,5,6-tetrafluoro-1,2-bis(bromomethyl)benzene.

A mixture of 3,4,5,6-tetrafluoro-1,2-bis(bromomethyl)-benzene (1.9 g, 6 mmol), m-phenoxybenzyl ester of valine (1.8 g, 6 mmol), potassium carbonate (1.7 g, 12 mmol) and 25 ml of THF/HMPT (1/1) is stirred for 3 days. Reaction is poured into ether (150 ml), and the organic phase is washed with water to neutral, dried over magnesium sulfate and evaporated under vacuum. The crude product is purified by prep. TLC on silica gel eluting with 10% ethyl acetate/hexane to obtain m-phenoxybenzyl 2-(4,5,6,7-tetrafluoro-2-isoindolinyl)-3-methylbutanoate, MS m/e 473 (M+).

EXAMPLE 5

To m-phenoxybenzyl 2-(2-isoindolinyl)-3-methylbutanoate (492 mg, 1.23 mmol) is added a solution of para-toluenesulfonic acid monohydrate (249 mg, 1.31 mmol) in 4 ml of 95% ethanol. The reaction mixture is allowed to stand for 2 hours at RT under nitrogen. The ethanol is removed under vacuum and the residue recrystallized from 30% hexane/benzene to yield the para-toluenesulfonic acid salt of m-phenoxybenzyl 2-(2-isoindolinyl)-3-methylbutanoate, m.p. 139°–140.3°.

EXAMPLE 6

To 5 ml HMPT is added the sodium salt of 2-bromo-3-methylbutanoic acid (1 g, 5.5 mmol) and 1,2,3,4-tetrahydroisoquinoline (1.84 g, 13.8 mmol). The reaction mixture is heated at 110° for 15 hours. After cooling, the reaction mixture is added to a mixture of ether and 5% NaOH. The aqueous phase is washed with ether (discarded) and the water is removed under vacuum to yield the sodium salt of 2-[2-(1,2,3,4-tetrahydroisoquinolinyl)]-3-methylbutanoic acid.

A mixture of the above prepared acid (5 mmol), potassium carbonate (0.69 g), m-phenoxybenzyl bromide (1.3 g) and DMF (15 ml) is stirred at RT for 18 hours. The reaction mixture is added to ether, and the organic phase is washed with water and brine, dried over sodium sulfate and solvent removed. The crude product is purified by prep. TLC on silica gel eluting with 20% ether/hexane to yield m-phenoxybenzyl 2-[2-(1,2,3,4-tetrahydroisoquinolinyl)]-3-methylbutanoate, MS m.e 415.2 (M+).

EXAMPLE 7

A. To valine (11.7 g, 0.10 mol) in 88% formic acid (40 ml) is added acetic formylanhydride (26.3 g, 0.30 mol) over 0.5 hr at 5°. The reaction mixture is warmed to 24° and stirred for 17 hours. The reaction is worked up by distilling off (bath temp. 45°–50°) the solvent, excess anhydride and acetic acid, to give, as a white solid, N-formylvaline, recrystallized from hot ethanol, m.p. 143°–145°.

B. To 8 g (0.055 mole) of the product of part A in 55 ml of HMPT is added m-phenoxybenzyl bromide (14.4 g, 0.055 mole) followed by anhydrous potassium carbonate (7.6 g, 0.055 mole). The reaction mixture is stirred, at 24°, for 48 hours and then worked up by pouring into ice-water (250 ml) and extracting with ether (3×100 ml). The combined ether extracts are washed with water (2×100 ml) and brine (25 ml) and dried over calcium sulfate and evaporated under vacuum to give the m-phenoxybenzyl ester of N-formylvaline.

C. To the ester (26 g, 0.0835 mole) of part B, in 84 ml of anhydrous methanol, is added 1 N methanolic HCl (92 ml, 0.092 mole). The reaction mixture is stirred at 24° for 18 hours and then the methanol removed under vacuum. The residue is poured into ice-water (200 ml) followed by removal of neutral impurities with ether. The aqueous layer is made basic by addition of 10% sodium bicarbonate and then extracted with ether (3×200 ml). The combined ether phases are washed with water (2×200 ml) until neutral and brine (100 ml) and then dried over calcium sulfate, filtered and rotoevaporated to give the m-phenoxybenzyl ester of valine nmr (CDCl₃) δ 0.91 [m, 6, (CH₃)₂CH], 1.37 (bs, 2, NH₂), 2.00 [m, 1, (CH₃)₂CH], 3.31

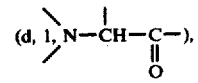

(d, 1, \N—CH—C—),
         /       ‖
                 O and 5.17 ppm (s, 2, ArCH₂O-). IR (film) ~3400 cm⁻¹ (NH₂), 1740 cm⁻¹ (C=O).

EXAMPLE 8

1-Chloro-2,3-dimethylbenzene (4.3 g, 31 mmol) is heated to 130° and irradiated with 150 watt incandescent lamp. Bromine (10.75 g, 67 mmol) is then slowly added to the hot solution with stirring over 30 minutes. After an additional 1 hour at 130° with irradiation, the solution is cooled and residual bromine and hydrogen bromide removed under vacuum to give 1,2-bis(bromomethyl)-6-chlorobenzene.

EXAMPLE 9

1,2-Bis(hydroxymethyl)-4-trifluoromethylbenzene (7 g, 34 mmol) is dissolved in 100 ml of benzene and diisopropylethylamine (17.6 g, 136 mmol) is added. The reaction mixture is cooled in an ice-bath and 7.4 ml (102 mmol) of thionyl chloride is added over about 20 minutes. The ice-bath is removed and the reaction mixture is stirred at RT for 4 hours. The reaction mixture is then diluted with hexane and the organic layer is washed with aqueous HCl and water, dried and the solvent removed under vacuum to give 1,2-bis(chloromethyl)-4-trifluoromethylbenzene.

EXAMPLE 10

A. α-Cyano-m-phenoxybenzyl alcohol (8.5 g, 38 mmol) is dissolved in 150 ml ether and cooled in an ice-bath. To the solution is slowly added methanesulfonyl chloride (5.4 g, 47 mmol) in 20 ml ether. After stirring about 20 minutes, triethylamine (4.76 g, 47 mmol) in 20 ml ether is added slowly and the mixture kept at 0° for 24 hours. Water is then added and the organic layer is separated, washed with 30% aqueous sodium bisulfite and water, dried and solvent removed under vacuum to yield α-cyano-m-phenoxybenzyl mesylate.

B. A mixture of 3,4,5,6-tetrafluoro-1,2-bis(bromomethyl)benzene (3 g, 9 mmol), valine (1 g, 9 mmol), potassium carbonate (2.8 g) and 25 ml THF/HMPT (1:1) is stirred for about 24 hours at RT (the reaction is followed by TLC). The reaction mixture is then diluted with 100 ml aqueous 10% KOH and extracted three times with ether. The aqueous phase is acidified to about pH 3 with aqueous HCl and extracted thoroughly with ether. The organic layer is washed with water, dried and solvent removed under vacuum to give 2-(4,5,6,7-tetrafluoro-2-isoindolinyl)-3-methylbutanoic acid.

C. To a stirred mixture of the above acid (2.3 g, 8 mmol), potassium carbonate (8 g) and 20 ml THF/DMF (1:1), under nitrogen, is slowly added α-cyano-m-phenoxybenzyl mesylate (2.4 g, 8 mmol) is 5 ml THF. The reaction mixture is stirred at RT overnight and then diluted with ether. The ether layer is separated, washed with water, dried and solvent removed under vacuum. The residue is purified by prep. TLC on silica gel (developing with 8% ethyl acetate in hexane) to give α-cyano-m-phenoxybenzyl 2-(4,5,6,7-tetrafluoro-2-isoindolinyl)-3-methylbutanoate.

EXAMPLE 11

To 20 ml DMF is added valine (1.17 g, 10 mmol) and potassium carbonate (5.5 g, 40 mmol) followed by α,α-dibromo-o-xylene (2.63 g, 10 mmol). The reaction mixture is stirred for about 20 hours at RT under nitrogen and then poured into ether and water. The aqueous layer is separated, acidified to about pH 3 with aqueous HCl and extracted thoroughly with ether. The organic layer is washed with water and brine, dried and solvent removed under vacuum to give 2-(2-isoindolinyl)-3-methylbutanoic acid.

To the above acid (1 g, 4.6 mmol) in 12 ml THF is added 8 ml of DMF and potassium carbonate (0.63 g, 5 mmol) followed by α-cyano-m-phenoxybenzyl mesylate (1.31 g, 5 mmol). The reaction mixture is stirred, under nitrogen, at RT for 20 hours. The reaction mixture is then diluted with ether. The organic layer is washed with water and brine, dried and solvent removed under vacuum. The residue is purified by prep. TLC to give α-cyano-m-phenoxybenzyl 2-(2-isoindolinyl)-3-methylbutanoate.

EXAMPLE 12

Following the procedures hereinabove (see Examples 4 and 8), each of 1,2-bis(bromomethyl)-4-bromobenzene, 1,2-bis(bromomethyl)-4-fluorobenzene, 1,2-bis(bromomethyl)-3-fluorobenzene, 1,2-bis(bromomethyl)-4-trifluoromethylbenzene, 1,2-bis(bromomethyl)-3,4-dichlorobenzene, 1,2-bis(bromomethyl)-3-trifluoromethylbenzene, 1,2-bis(bromomethyl)-3-nitrobenzene, and 1,2-bis(bromomethyl)-4-methoxybenzene is prepared and reacted with the m-phenoxybenzyl ester of valine to give:

m-phenoxybenzyl 2-(5-bromo-2-isoindolinyl)-3-methylbutanoate,
m-phenoxybenzyl 2-(5-fluoro-2-isoindolinyl)-3-methylbutanoate,
m-phenoxybenzyl 2-(4-fluoro-2-isoindolinyl)-3-methylbutanoate,
m-phenoxybenzyl 2-(5-trifluoromethyl-2-isoindolinyl)-3-methylbutanoate,
m-phenoxybenzyl 2-(4,5-dichloro-2-isoindolinyl)-3-methylbutanoate,
m-phenoxybenzyl 2-(4-trifluoromethyl-2-isoindolinyl)-3-methylbutanoate,
m-phenoxybenzyl 2-(4-nitro-2-isoindolinyl)-3-methylbutanoate, and
m-phenoxybenzyl 2-(5-methoxy-2-isoindolinyl)-3-methylbutanoate.

The α-cyano-m-phenoxybenzyl esters of the above are prepared using the procedure of Example 10 by reacting, e.g. 1,2-bis(bromomethyl)-3-trifluoromethylbenzene with valine to prepare 2-(4-trifluoromethyl-2-isoindolinyl)-3-methylbutanoic acid and esterifying using α-cyano-m-phenoxybenzyl mesylate.

EXAMPLE 13

A mixture of m-phenoxybenzyl 2-(4,5,6,7-tetrafluoro-2-isoindolinyl)-3-methylbutanoate (0.4 g), potassium hydroxide (0.134 g), ethanol (8 ml) and water (2 ml) is heated to reflux for 4 hours. After cooling, the reaction mixture is concentrated under vacuum and 50 ml of water is added. This mixture is washed with ether (3×). The aqueous phase is carefully adjusted to pH 7 and then extracted with ether (3×). The combined ether extracts are washed with water, dried and solvent removed under vacuum to yield 2-(4,5,6,7-tetrafluoro-2-isoindolinyl)-3-methylbutanoic acid, a white powder.

A mixture of the above prepared acid (0.1 g), potassium bicarbonate (0.034 g) in 5 ml of THF/DMF (1:1) is stirred for about 15 minutes and then α-cyano-m-phenoxybenzyl mesylate (0.1 g) in 7 ml of THF/DMF (1:1) is added. The reaction mixture is stirred for about 52 hours. Then the reaction is worked up by diluting with ether (about 75 ml), washing with water and sat. NaCl, drying and evaporating under vacuum to remove solvent to yield crude product, which is chromatographed by prep. TLC on silica gel plates eluting with 10% ethyl acetate/hexane to give α-cyano-m-phenoxybenzyl 2-(4,5,6,7-tetrafluoro-2-isoindolinyl)-3-methylbutanoate, colorless viscous liquid, MS m/e 498 (M+).

EXAMPLE 14

Following the procedure of Example 4, 3,4,5,6-tetrachloro-1,2-bis(hydroxymethyl)benzene is reacted with phosphorus tribromide to yield 3,4,5,6-tetrachloro-1,2-bis(bromomethyl) benzene. The thus-obtained di-bromide is reacted with m-phenoxybenzyl ester of valine according to the procedure of Example 4 to yield m-phenoxybenzyl 2-(4,5,6,7-tetrachloro-2-isoindolinyl)-3-methylbutanoate.

The ester, m-phenoxybenzyl 2-(4,5,6,7-tetrachloro-2-isoindolinyl)-3-methylbutanoate is hydrolyzed to 2-(4,5,6,7-tetrachloro-2-isoindolinyl)-3-methylbutanoic acid using KOH in ethanol/water, which is reacted with α-cyano-m-phenoxybenzyl mesylate to yield α-cyano-m-phenoxybenzyl 2-(4,5,6,7-tetrachloro-2-isoindolinyl)-3-methylbutanoate.

EXAMPLE 15

3,6-Difluoro-4,5-dichloro-1,2-bis(bromomethyl)benzene (prepared from the diol by treatment with phosphorus tribromide) is reacted with m-phenoxybenzyl ester of valine to yield m-phenoxybenzyl 2-(4,7- difluoro-5,6-dichloro-2-isoindolinyl)-3-methylbutanoate.

A mixture of m-phenoxybenzyl 2-(4,7-difluoro-5,6-dichloro-2-isoindolinyl)-3-methylbutanoate (0.38 g), KOH (0.134 g), ethanol (8 ml) and water (2 ml) is heated to reflux for 14 hours. After cooling, the reaction is concentrated under vacuum and about 50 ml of water added. The mixture is washed with ether. The aqueous phase is adjusted to pH 7 and then the water is removed by evaporation to yield 2-(4,7-difluoro-5,6-dichloro-2-isoindolinyl)-3-methylbutanoic acid.

The foregoing acid is reacted with α-cyano-m-phenoxybenzyl mesylate to yield the ester, α-cyano-m-phenoxybenzyl 2-(4,7-difluoro-5,6-dichloro-2-isoindolinyl)-3-methylbutanoate.

Young lima bean leaves (in water) infested with approximately 50 adult *Tetranychus urticae* are sprayed to runoff with test compound 4 [m-phenoxybenzyl 2-(4,5,6,7-tetrafluoro-2-isoindolinyl)-3-methylbutanoate] diluted to three different concentrations in aqueous carrier containing 0.025% Tween 20 and 0.1% wetting agent. The treated leaves are maintained at 24° and 16 hr photoperiod for 2 days. Live adult mites are then counted and substracted from the original total to obtain the number affected, which is stated as a percentage of the total. Correction is made for any control mortality using Abbott's formula. The compound had an $LC_{50}$ of less than 10 ppm (parts per million).

Individual fava bean leaves are dipped in test compound 4 diluted to three different concentrations in acetone with 0.025% Tween 20 and 0.1% wetting agent. The leaves are allowed to dry for 2 hours, then infested with 10 adult *Aphis fabae* caged on the upper surface of the leaves. The treated leaves are maintained for 48 hours at 24° and 16 hr photoperiod. The effect is stated as the number dead calculated as a percentage of the total aphids. This is corrected for control mortality, if any, using Abbott's formula. The compound had an $LC_{50}$ of less than 5 ppm.

Fifteen 72-hour-old adult female *Musca domestica* L. are anesthetized with ether vapor. These are then treated with 1 ul of test compound 2 [m-phenoxybenzyl 2-(5-chloro-2-isoindolinyl)-3-methylbutanoate] diluted to three different concentrations in acetone applied to the dorsal surface of the prothorax. They are held in an assay container with milk-saturated cotton at 25°, 16 hr photoperiod for 24 hours. The effect is stated as the number dead calculated as a percentage of the total, corrected for any control mortality using Abbott's formula. The compound gave an $LC_{50}$ of less than 0.01%.

Into a mixture of 45 mg of wettable powder [Attaclay (60%), Marosperse N-22 (26.7%) and Igepon T-77 (13.3%)] and 0.5 ml of water containing the test compound 4 at three different concentrations is dipped fifteen fed tick nymphs (*Ornithodoros nymph I*). The treated numphs are maintained on filter paper for 7 days at 28°, 64% humidity, 16 hr photoperiod and then observed. Correction is made for any mortality in the control using Abbott's formula. The $LC_{50}$ of the compound was less than 6 ppm.

Two groups of 10 each of 0-24 hour II instar *Heliothis virescens* larvae were treated with 1 ul of each of test compound 2 and 4 in acetone at three different concentrations by application to the dorsum of the thorax. Two groups of 10 each are treated identically with 1 ul acetone as controls. Larvae are held individually in 30 ml plastic cups provided with artificial medium for 72 hours at 25° and 16 hr photoperiod. After 72 hr the number of dead is calculated as a percentage of the total number originally treated and then corrected for any mortality in the control groups using Abbott's formula. The $LC_{50}$ of each compound was less than 0.5%.

A 4E emulsive concentrate was prepared using the p-toluenesulfonic acid salt of m-phenoxybenzyl 2-(2-isoindolinyl)-3-methylbutanoate (51.3%), Atlox 3404F (3%), Atlox 3403F (3%) and Tenneco 500-100 (42.7%), was diluted with water and applied to *Tetranychus urticae* as described above. The $LC_{50}$ value was less than 10 ppm.

What is claimed is:

1. A compound of the formula:

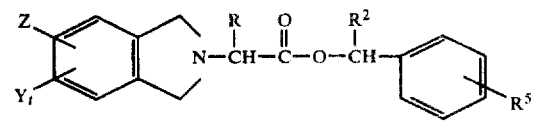

wherein,

R is isopropyl;

$R^2$ is hydrogen, cyano, methyl or ethynyl;

$R^5$ is phenoxy;

Z is hydrogen, bromo, chloro or fluoro;

Y is bromo, chloro, fluoro or trifluoromethyl; and t is zero, one, two or three; and the salts thereof of strong inorganic acids or organic acids.

2. A compound according to claim 1 wherein $R^2$ is hydrogen or cyano and Z is hydrogen.

3. A compound according to claim 2 wherein t is zero, one or two.

4. A compound according to claim 3 wherein t is one.

5. A compound according to claim 1 wherein each of Y and Z is bromo, fluoro or chloro and t is three.

6. The p-toluenesulfonic acid salt of m-phenoxybenzyl 2-(2-isoindolinyl)-3-methylbutanoate, according to claim 1.

7. The compound, m-phenoxybenzyl 2-(5-chloro-2-isoindolinyl)-3-methylbutanoate, according to claim 1.

8. A compound of the formula:

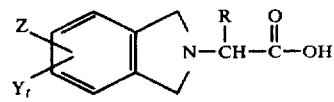

wherein,

R is isopropyl;

Z is hydrogen, bromo, chloro or fluoro;

Y is bromo, chloro, fluoro or trifluoromethyl; and t is zero, one, two or three.

9. A compound according to claim 8 wherein Z is hydrogen and t is zero, one or two.

10. A compound according to claim 9 wherein t is zero or one.

11. A compound according to claim 8 wherein each of Y and Z is bromo, chloro or fluoro and t is two.

12. A compound according to claim 8 wherein each of Y and Z is bromo, chloro or fluoro and t is three.

13. The compound, 2-(2-isoindolinyl)-3-methylbutanoic acid, according to claim 8.

14. The compound, 2-(4-trifluoromethyl-2-isoindolinyl)-3-methylbutanoic acid, according to claim 8.

15. The compound, 2-(4,5,6,7-tetrachloro-2-isoindolinyl)-3-methylbutanoic acid, according to claim 8.

16. The compound, m-phenoxybenzyl 2-(4,5,6,7-tetrafluoro-2-isoindolinyl)-3-methylbutanoate, according to claim 1.

17. The compound α-cyano-m-phenoxybenzyl 2-(4,5,6,7-tetrafluoro-2-isoindolinyl)-3-methylbutanoate, according to claim 1.

18. The compound, 2-(4,5,6,7-tetrafluoro-2-isoindolinyl)-3-methylbutanoic acid, according to claim 8.

* * * * *